United States Patent [19]

Sakakura

[11] Patent Number: 5,386,052

[45] Date of Patent: Jan. 31, 1995

[54] PROCESS FOR PRODUCING ACRYLIC OR METHACRYLIC ESTERS

[75] Inventor: Yasuyuki Sakakura, Yokkaichi, Japan

[73] Assignee: Mitsubishi Petrochemical Company Limited, Tokyo, Japan

[21] Appl. No.: 220,019

[22] Filed: Mar. 30, 1994

[30] Foreign Application Priority Data

Mar. 31, 1993 [JP] Japan .................. 5-108674

[51] Int. Cl.6 ............................................ C07C 69/52
[52] U.S. Cl. .................................................. 560/205
[58] Field of Search ......................................... 560/205

[56] References Cited

U.S. PATENT DOCUMENTS

| 4,474,981 | 10/1984 | Katoh et al. | 560/205 |
|---|---|---|---|
| 4,675,436 | 6/1987 | Dietrich et al. | 560/205 |
| 4,889,950 | 12/1989 | Bott et al. | 560/205 |
| 4,968,834 | 11/1990 | Smith et al. | 560/205 |
| 5,187,309 | 2/1993 | Esch et al. | 560/218 |

FOREIGN PATENT DOCUMENTS

| 255773 | 2/1988 | European Pat. Off. . |
|---|---|---|
| 566047 | 10/1993 | European Pat. Off. . |
| 2509294 | 1/1983 | France . |
| 1249857 | 9/1967 | Germany . |
| 3021114 | 2/1978 | Japan . |
| 959880 | 6/1964 | United Kingdom . |

*Primary Examiner*—Paul J. Killos
*Attorney, Agent, or Firm*—Armstrong, Westerman, Hattori, McLeland & Naughton

[57] ABSTRACT

There is provided a process for producing an acrylic or methacrylic ester, comprising the steps of:

(a) reacting acrylic or methacrylic acid with an alcohol having 4 or more-carbon atoms in the presence of an acid catalyst to synthesize the corresponding ester;

(b) washing the reaction liquid obtained in step (a) with water, followed by separation into the reaction liquid and an aqueous solution containing the acid catalyst; and (c) recycling the aqueous solution obtained in step (b) to step (a).

6 Claims, No Drawings

PROCESS FOR PRODUCING ACRYLIC OR METHACRYLIC ESTERS

BACKGROUND OF THE INVENTION

1. Field of the Invention

This invention relates to an improved process for producing acrylic or methacrylic esters. More particularly, this invention provides an industrially advantageous process for producing acrylic or methacrylic esters in which an acid catalyst used for esterification reaction is efficiently recovered and reused.

2. Background Art

For the industrial production of acrylic or methacrylic esters from acrylic or methacrylic acid and alcohols having 4 or more carbon atoms, the method in which the esterification reaction is carried out by using a strong acid as a catalyst, as described in, for instance, Japanese Laid-Open Patent Publication No. 271247/1986, has been conventionally employed.

The esterification reaction between acrylic or methacrylic acid and an alcohol having 4 or more carbon atoms is an equilibrium reaction. Therefore, the conversion in the reaction cannot exceed a certain degree which is determined by an equilibrium constant. In order to increase the degree of conversion in the reaction, it is necessary to use a large excess of either one of acrylic (or methacrylic) acid and an alcohol (German Patent No. 2548561), or to remove water (reaction water) produced in the reaction from the reaction mixture. The removal of the reaction water is usually effected by distillation. A third component may be added as an azeotropic agent in order to increase the efficiency of the distillation (Japanese Patent Publication No. 41663/1987).

As the strong acids for use as a catalyst, there may be mentioned sulfuric acid, p-toluenesulfonic acid, benzenesulfonic acid, xylenesulfonic acid, naphthenesulfonic acid, methanesulfonic acid, etc. These stong acids must be removed from the reaction liquid after the reaction is completed.

As a post-treatment method for removing the strong acid, there has been proposed a method in which the reaction liquid is treated with an aqueous alkaline solution for neutralization (Japanese Laid-Open Patent Publications Nos. 243046/1986, 34965/1991 and 230240/1992). According to this method, a large amount of alkali is needed for effecting a sufficient neutralization. Moreover, it is very difficult to separate and recover the acid catalyst and unreacted acrylic or methacrylic acid from the aqueous alkaline solution after the treatment and, therefore, the aqueous alkaline solution must be disposed as a waste after the treatment. This method thus has the drawback of the production of a large amount of waste water which contains the harmful organic acid salt at a high concentration.

An object of the present invention is to provide a process for the production of acrylic or methacrylic esters which enables the reuse of an acid catalyst and which overcomes the problem of organic salt-containing waste water encountered in the above prior art.

SUMMARY OF THE INVENTION

The above object can be achieved, according to the present invention, by a process for producing an acrylic or methacrylic ester, comprising the steps of:

(a) reacting acrylic or methacrylic acid with an alcohol having 4 or more carbon atoms in the presence of an acid catalyst to synthesize the corresponding ester;

(b) washing the reaction liquid obtained in step (a) with water, followed by separation into the reaction liquid and an aqueous solution containing the acid catalyst; and (c) recycling the aqueous solution obtained in step (b) to step (a).

According to the present invention, the acid catalyst used for the esterification reaction and unreacted acrylic or methacrylic acid can be effectively recovered and reused for the reaction. Thus, the amount of catalyst to be used can be considerably reduced. Moreover, since the content of the acid catalyst and meth(acrylic) acid in the reaction liquid is very low after the washing with water, there is little or no need for an additional treatment of the reaction liquid with an alkali, meaning that the production of a large amount of waste water containing the harmful organic salt can be avoided.

DETAILED DESCRIPTION OF THE INVENTION

In the present invention, any alcohol selected from aliphatic, alicyclic and aromatic alcohols can be used as the alcohol having 4 or more carbon atoms. Examples of the aliphatic alcohols include butyl alcohol, pentyl alcohol, hexyl alcohol, heptyl alcohol, octyl alcohol, 2-ethylhexyl alcohol, nonyl alcohol, decyl alcohol, dodecyl alcohol, hexadecyl alcohol and stearlyl alcohol. Examples of the alicyclic alcohols include cyclopentyl alcohol, cyclohexyl alcohol, methylcyclohexyl alcohol, ethylcyclohexyl alcohol and butylcyclohexyl alcohol. Examples of the aromatic alcohols include benzyl alcohol, methylbenzyl alcohol, dimethylbenzyl alcohol and butylbenzyl alcohol.

As the acid catalyst for esterification, toluenesulfonic acid, benzenesulfonic acid, xylenesulfonic acid and methanesulfonic acid are preferably used. Conventionally, sulfuric acid has frequently been used as a catalyst for the esterification. This acid, however, is not suited as a catalyst for use in the present invention for the following reasons: When used as a catalyst, sulfuric acid is present in the reaction liquid after esterification as an alkylsulfuric acid, which cannot be efficiently extracted with a small amount of water. Thus, a large amount of water is need for an adequate extraction of the acid. When the aqueous solution after extraction is recycled to an esterification reactor, the large amount of water will adversely affect the reaction. Moreover, since the aqueous solution of sulfuric acid is very corrosive, facility troubles tend to occur.

In the esterification reaction between acrylic or methacrylic acid and an alcohol with 4 or more carbon atoms carried out in the presence of an acid catalyst, the starting acrylic or methacrylic acid and the alcohol in the molar ratio of 1.0:1.2–1.0:0.8 are usually supplied to a reactor. The amount of the acid catalyst used is generally from 0.1 to 5.0% by weight, preferably from 0.5 to 2.0% by weight of the reactants. The reaction is carried out generally at a temperature of 70° to 180° C. while reaction water produced in the course of esterification is preferably removed by distillation or azeotropic distillation (reaction-distillation method). In order to facilitate the removal of reaction water, an inert azeotropic agent may be used. Hydrocarbons such as benzene, toluene and cyclohexane are commonly used as the azeotropic agent. The removal of reaction water may also be conducted by means of membrane separation using a vapor separation membrane or a pervaporation membrane, or by a method other than distillation. In order to prevent the loss of acrylic or methacrylic acid or the ester due to the occurrence of unfavorable polymerization thereof, a polymerization inhibitor or an oxygen-containing gas is usually added to a reactor.

The reaction liquid discharged from the reactor after the esterification reaction is completed contains unreacted alcohol and acrylic or methacrylic acid, the corresponding ester and, if used, an azeotropic agent as main components, and a strong acid as a catalyst and a trace amount of polymerization inhibitor.

The reaction liquid is preferably cooled to a temperature of 10° to 60° C., and then washed with water for extraction. The temperature of the wash water is preferably the same as or somewhat lower than the temperature of the reaction liquid. The weight ratio of the wash water to the reaction liquid is preferably 0.5 or less, more preferably from 0.05 to 0.2. Although fresh water can be used as the wash water, the reaction water produced in the esterification reaction and removed from the reaction system may also be employed. The use of the latter has the advantage that the amount of waste water can be reduced.

The washing with water can be conducted in various manners. There may be mentioned, for example, a manner in which water and the reaction liquid are mixed under agitation, and then the mixture is allowed to stand to separate the aqueous phase from the reaction liquid and a manner in which both the washing and the liquid-liquid separation are conducted by means of a centrifuge. The washing is most effectively conducted by means of an extraction column. In the case of the above mentioned stirring/allowing to stand manner, it is sometimes difficult to obtain the liquid-liquid separation because an emulsion of the reaction liquid and the wash water is formed due to the strong stirring force applied thereto. In contrast, when the water washing is conducted in an extraction column, the liquid-liquid contact is effected with the application of a weak stirring force, so that the emulsion can hardly be formed and thus the liquid-liquid separation can be readily conducted.

An extraction column of an ordinary type can be used. The common system is as follows: the reaction liquid is fed into the extraction column from the lower part thereof, and water from the upper part of the column; while the reaction liquid from which the catalyst and acrylic or methacrylic acid are removed is obtained from the top of the column, and an aqueous solution containing the catalyst and acrylic or methacrylic acid from the bottom of the column. A packed column, a tray tower or the like is usually used as an extraction column. It is preferred to use an apparatus an which the liquid-liquid contact is effected with high efficiency.

The reaction liquid washed with water as described above is, if necessary, further washed with water or with an aqueous alkaline solution to completely remove the remaining catalyst and the acid, followed by purification by means of distillation or the like, thereby obtaining an acrylic or methacrylic ester.

On the other hand, the wash water after the washing is an aqueous solution containing the catalyst and acrylic or methacrylic acid. The catalyst content in the aqueous solution is generally from 3 to 20% by weight. The rate of removal of the catalyst from the reaction liquid is, in general, 60% or more, and it is as high as 80 to 95% when an extraction column is employed. The aqueous solution is recycled back to the esterification reaction step, and the catalyst is effectively reused for the reaction.

The important point here is the influence upon the reaction of the recycling of water to the reaction system. In this respect, it has been the commen understanding in the art that since the esterification reaction is an equilibrium reaction, the addition of water even in a small amount to the reaction system will exert an adverse influence on the reaction and significantly lower the degree of conversion. However, it has been unexpectedly found by the present inventor that the addition of water has no substantial influence on the reaction when water is added at the initial stage of reaction and in a small amount, especially when the reaction is conducted in the above described reaction-distillation manner. When the amount of water recycled to the reaction system is large, such as in the case where the weight ratio of the wash water to the reaction liquid in the water washing is more than 0.5, there may occur a considerable drop in the reaction rate upon the water addition to the system. In that case, the removal of water from the reaction system should be accelerated if the reaction is conducted in the reaction-distillation manner. Further, it is possible and is especially preferred when a large amount of water is employed in the water washing step, to concentrate the aqueous solution after washing by evaporating at least a part of water before it is recycled to the reaction system. The evaporation of water may be carried out, for example, by means of a distillation column that is fixed on a reactor in the case where the reaction is conducted in the reaction-distillation manner. Thus, in this case, the aqueous solution after washing is not directly recycled to the reactor, but to the distillation column fixed on the reactor. At any rate, in view of the consumption of time and energy required for evaporation of water, the amount of water to be used in the water washing step should not be too large.

The following examples further illustrate the present invention but are not intended to limit it.

Example 1

86.1 kg of methacrylic acid, 88.9 kg of isobutyl alcohol (the molar ratio of isobutyl alcohol to methacrylic acid: 1.2), 1.3 kg of xylenesulfonic acid as an esterification catalyst and 500 ppm by weight of hydroquinone as a polymerization inhibitor were supplied to a reactor equipped with a distillation column. The reactor was heated by steam to adjust the reaction temperature to 100° C. The reaction was carried out under reduced pressure. While the reaction was proceeding, the vapor generated was introduced into the distillation column. The distillate flowing from the top of the distillation column was separated into the aqueous phase and the oil phase; the oil phase was refluxed to the distillation column, while the aqueous phase was drawn out. In this manner, the reaction water produced in the esterification reaction was removed from the reaction system.

The heating of the reactor was continued until the reaction was completed and no reaction water was produced any more. The time required for the reaction was 6.5 hours. The amount of the reaction water removed from the reaction system was 18.6 kg. The reaction water was found to contain approximately 6% by weight of i-butanol.

The reaction liquid was drawn out from the reactor. As a result of analysis by gas chromatography, the reaction liquid was found to contain 88.3% by weight of isobutyl methacrylate and 9.6% by weight of isobutyl alcohol. The degree of conversion of methacrylic acid was 98% by weight. The reaction liquid was further analyzed by liquid chromatography. As a result, it was found that the concentration of xylenesulfonic acid was 0.82%.

The xylenesulfonic acid was separated from the reaction liquid by extraction using the above reaction water as extraction water. A packed column with a diameter of 10 cm was used as an extraction column. The column was packed with Raschig rings having an outer diameter of 8 mm, the height of the packing layer being 90 cm. The reaction liquid and the extracton water both at 25° C. were fed into the column. The weight ratio of the reaction liquid to the extraction water was adjusted to 1:0.2. After the extraction was completed, the concentration of xylenesulfonic acid in the extraction water was found to be 3.3% by weight. The rate of recovery of xylenesulfonic acid was 80% by weight. The aqueous solution containing the xylenesulfonic acid was recycled to the reactor.

Using as a catalyst 1.04 g of xylenesulfonic acid that was contained in the aqueous solution recycled and 0.26 g of newly added xylenesulfonic acid, esterification reaction was conducted under otherwise the same conditions as the above described esterification reaction. The degree of conversion of methacrylic acid was again 98% by weight. The time required for this reaction was the same as before.

Example 2

This example illustrates the synthesis of octyl acrylate from acrylic acid and octyl alcohol carried out in a continuous manner.

16 g/hr of p-toluenesulfonic acid as a catalyst, 500 ppm by weight/hr of phenothiazine as a polymerization inhibitor, 716 g/hr of octyl alcohol, 360 g/hr of acrylic acid and 109 g/hr of toluene as an azeotropic agent were continuously supplied to a reactor equipped with a distillation column. The reactor was heated in an oil bath, and the reaction temperature was maintained at 110° C. and the pressure at 120 tor. Esterification reaction was carried out while the reaction water produced was removed from the reaction system in the same manner as described in Example 1.

The reaction liquid was continuously drawn out from the reactor in such an amount as to keep the amount of the liquid contained in the reactor at 5 liters. The amount of the reaction liquid drawn out was 1115 g/hour. The reaction liquid was found to contain 10% by weight of octyl aclcohol, 2.2% by weight of acrylic acid, 77.9% by weight of octyl acrylate, 9.8% by weight of toluene, and 1.4% by weight of p-toluenesulfonic acid. The reaction water continuously recovered from the distillation column was found to contain 1.2% by weight of acrylic acid. The degree of conversion of acrylic acid was 93% by weight.

The reaction liquid was cooled to room temperature (25° C.), and then fed into an extraction column from the lower part thereof. The reaction water recovered from the distillation column was continuously fed at 25° C., as extraction water, into the extraction column from the upper part thereof. The weight ratio of the reaction liquid to the extraction water was 1.0: 0.1. The extraction column used was one made of glass, having a diameter of 3 cm. The column was packed with Raschig rings, the height of the packing layer being 50 cm. From the bottom of the extraction column, 121 g/hr of an aqueous solution containing 2.9% by weight of acrylic acid and 12.5% by weight of p-toluenesulfonic acid was obtained. The rate of recovery of p-toluenesulfonic acid was 95% by weight. The aqueous solution containing the p-toluenesulfonic acid was continuously supplied to the central part of the distillation column on the reactor. The reaction was continued, while the amount of p-toluenesulfonic acid newly added was reduced to 0.8 g/hr and the heating of the reactor was strengthened so as to maintain the concentration of water in the reaction system at 0.1% by weight or less. The degree of conversion of acrylic acid was found to be unchanged.

What is claimed is:

1. A process for producing an acrylic or methacrylic ester, comprising the steps of:
   (a) reacting acrylic or methacrylic acid with an alcohol having 4 or more carbon atoms in the presence of an acid catalyst to synthesize the corresponding ester;
   (b) washing the reaction liquid obtained in step (a) with water, followed by separation into the reaction liquid and an aqueous solution containing the acid catalyst; and
   (c) recycling the aqueous solution obtained in step (b) to step (a).

2. The process according to claim 1, wherein the acid catalyst is selected from the group consisting of methanesulfonic acid, benzenesulfonic acid, toluenesulfonic acid and xylenesulfonic acid.

3. The process according to claim 1, wherein the weight ratio of water to the reaction liquid in step (b) is 0.5 or less.

4. The process according to claim 1, wherein the washing of the reaction liquid with water is conducted after the reaction liquid is cooled to a temperature of 10° to 60° C.

5. The process according to claim 1, wherein step (b) is carried out in an extraction column.

6. The process according to claim 1, wherein the aqueous solution containing the acid catalyst is recycled after it is concentrated by evaporating at least a part of water contained therein.

* * * * *